United States Patent
Ohno et al.

(10) Patent No.: US 7,138,553 B2
(45) Date of Patent: Nov. 21, 2006

(54) METHOD FOR PURIFYING TETRACHLOROETHYLENE AND PROCESS FOR PRODUCING HYDROFLUOROCARBONS

(75) Inventors: Hiromoto Ohno, Kawasaki (JP); Toshio Ohi, Kawasaki (JP); Makoto Miyamura, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 150 days.

(21) Appl. No.: 10/363,639

(22) PCT Filed: Jul. 5, 2002

(86) PCT No.: PCT/JP02/06860

§ 371 (c)(1), (2), (4) Date: Mar. 4, 2003

(87) PCT Pub. No.: WO03/004445

PCT Pub. Date: Jan. 16, 2003

(65) Prior Publication Data
US 2003/0191350 A1    Oct. 9, 2003

Related U.S. Application Data

(60) Provisional application No. 60/374,812, filed on Apr. 24, 2002, provisional application No. 60/368,966, filed on Apr. 2, 2002, provisional application No. 60/306,423, filed on Jul. 20, 2001.

(30) Foreign Application Priority Data

Jul. 6, 2001 (JP) ............................ 2001-206882
Mar. 26, 2002 (JP) ............................ 2002-086500
Apr. 19, 2002 (JP) ............................ 2002-117341

(51) Int. Cl.
C07C 17/00 (2006.01)
C07C 19/08 (2006.01)

(52) U.S. Cl. ...................... 570/164; 570/169; 570/174; 570/178

(58) Field of Classification Search ................ 570/164, 570/169, 175, 178
See application file for complete search history.

(56) References Cited

U.S. PATENT DOCUMENTS 3,751,494 A    8/1973    Beckers 4,765,876 A    8/1988    Masini et al.
5,847,244 A  * 12/1998   Shibanuma et al. ........ 570/169
5,959,166 A    9/1999    Kim et al.

FOREIGN PATENT DOCUMENTS

| EP | 0 101 047 A | 2/1984 |
|---|---|---|
| EP | 0 648 726 A | 4/1995 |
| EP | 0 687 660 A | 12/1995 |
| JP | 6-321819 A | 11/1994 |
| WO | WO 93/25505 A | 12/1993 |

OTHER PUBLICATIONS

International Search Report, PCT/JP02/06860 dated Jul. 5, 2002.
Patent Abstracts of Japan, abstracting JP-A-6-321819, dated Nov. 22, 1994.
Satake, et al. "Solvent recovery by activated carbon fiber", Chemical Abstracts Service, STN Database Accession No. 109:95073 CA (1988).
Database WPI, Section Ch, Week 199348, Derwent Publications Ltd., AN 1993-383008 for JP-A-5-286875 (Nov. 2, 1993).
Database WPI, Section Ch, Week 199812, Derwent Publications Ltd., AN 1998-126108 for JP-A-10-7603 (Jan. 13, 1998).
Database WPI, Section Ch, Week 199607, Derwent Publications Ltd., AN 1996-065445 for JP-A-7-324044 (Dec. 12, 1995).

* cited by examiner

*Primary Examiner*—Sikarl A. Witherspoon
(74) *Attorney, Agent, or Firm*—Sughrue Mion, PLLC (57) ABSTRACT

Tetrachloroethylene containing a stabilizer is contacted with a zeolite having an average pore size of 3.4 to 11 Å and/or a carbonaceous adsorbent having an average pore size of 3.4 to 11 Å in a liquid phase to obtain a high purity tetrachloroethylene. A halogenated alkene and/or a halogenated alkane are reacted with hydrogen fluoride in the presence of a fluorination catalyst to produce a first hydrofluorocarbon, a halogenated alkene and/or a halogenated alkane are reacted with hydrogen fluoride in the presence of a fluorination catalyst to produce a second hydrofluorocarbon, and the products are joined and then distilled to obtain the first and second hydrofluorocarbons.

36 Claims, 2 Drawing Sheets

METHOD FOR PURIFYING TETRACHLOROETHYLENE AND PROCESS FOR PRODUCING HYDROFLUOROCARBONS

CROSS-REFERENCE TO RELATED APPLICATIONS

This application is a 371 of PCT/JP02/06860 filed Jul. 5, 2002, and published as WO 03/004445 on Jan. 16, 2006.

This application is an application filed under 35 U.S.C. §111(a) claiming benefit pursuant to 35 U.S.C. §119(e)(1) of the filing date of the Provisional Application No. 60/306,423 filed Jul. 20, 2001, the filing date of the Provisional Application No. 60/368,966 filed Apr. 2, 2002, and the filing date of the Provisional Application No. 60/374,812 filed Apr. 24, 2002, pursuant to 35 U.S.C. §111(b).

TECHNICAL FIELD

The present invention relates to a method for purifying tetrachloroethylene and a process for producing a hydrofluorocarbon.

BACKGROUND ART

As for the production of tetrachloroethylene ($CCl_2=CCl_2$) (hereinafter sometimes referred to as "PCE"), for example, (1) a method of thermally decomposing carbon tetrachloride, (2) a method of simultaneously conducting chlorination and dehydrochlorination of a chloroolefin, and (3) a method of using chlorine and a hydrocarbon such as natural gas or LPG as starting materials are known. In the methods, a stabilizer is added so as to ensure the stability of tetrachloroethylene and, in general, the stabilizer is added in an amount of hundreds to thousands of ppm. As for uses, tetrachloroethylene is used, for example, as a dry cleaning solvent, a starting material for the production of a fluorocarbon gas, or a solvent.

On the other hand, as for the production of pentafluoroethane ($CF_3CHF_2$), for example, (1) a method of fluorinating tetrachloroethylene or a fluorinated product thereof with hydrogen fluoride (see, Japanese International Application Domestic Publication No. 9-511515, etc.), (2) a method of hydrogenolyzing chloropentafluoroethane ($CClF_2CF_3$) (see, Japanese Unexamined Patent Publication No. 5-97728 (JP-A-5-97728), etc.) and (3) a method of reacting a fluorine gas with halogen-containing ethylene (see, Japanese Unexamined Patent Publication No. 1-38034 (JP-A-1-38034)) are known.

For example, in the method of producing pentafluoroethane by reacting tetrachloroethylene with hydrogen fluoride in a gas phase in the presence of a fluorination catalyst, the reaction is conducted through two steps different in reaction conditions. More specifically, this method comprises a first reaction where tetrachloroethylene and hydrogen fluoride (HF) are reacted in a gas phase in the presence of a fluorination catalyst to mainly produce 1,1-dichloro-2,2,2-trifluoroethane ($CHCl_2CF_3$) and 1-chloro-1,2,2,2-tetrafluoroethane ($CHClFCF_3$), and a second reaction where the product mainly composed of $CHCl_2CF_3$ and $CHClFCF_3$ produced in the first reaction is reacted with HF in a gas phase in the presence of a fluorination catalyst to mainly produce pentafluoroethane.

In this method, tetrachloroethylene as one of starting materials for the first reaction contains a stabilizer usually on the order of tens to hundreds of mass ppm so as to prevent, for example, the generation of an acid content due to decomposition. For example, a hydroxyl group-containing aromatic compound, such as phenol or cresol, is contained and if such a stabilizer is not contained in tetrachloroethylene, the tetrachloroethylene lacks in stability and a side reaction such as generation of an acid content proceeds.

However, the stabilizer contained in tetrachloroethylene gives rise to deterioration of the activity of a catalyst used for the production of pentafluoroethane. Therefore, a stabilizer is preferably not contained. This may be attained, for example, by removing the stabilizer before the first reaction. However, conventional removing methods by fractional distillation or the like have a problem in that the operation is cumbersome and the equipment therefor is expensive.

Further, hydrofluorocarbons (hereinafter sometimes referred to as "HFC") have an ozone depletion potential of 0. Among hydrofluorocarbons, pentafluoroethane (hereinafter sometimes referred to as "HFC-125") and 1,1,1,2-tetrafluoroethane (hereinafter sometimes referred to as "HFC-134a") are useful compounds, for example, as refrigerants.

As for the production of pentafluoroethane, for example, a method of reacting hydrogen fluoride with tetrachloroethylene, 2,2-dichloro-1,1,1-trifluoroethane (hereinafter sometimes referred to as "HCFC-123") or 2-chloro-1,1,1,2-tetrafluoroethane (hereinafter sometimes referred to as "HCFC-124") in the presence of a fluorination catalyst is known.

Also, a method of obtaining pentafluoroethane through two steps of reacting hydrogen fluoride with tetrachloroethylene in the presence of a fluorination catalyst to produce an intermediate product gas mainly comprising HCFC-123 and/or HCFC-124 which are intermediates of pentafluoroethane, and reacting hydrogen fluoride with the gas containing these intermediates in the presence of a fluorination catalyst to obtain pentafluoroethane, may be used. More specifically, a process of reacting hydrogen fluoride with tetrachloroethylene, shown by the following formula 1 and/or formula 2 is conducted in a first reactor to produce an intermediate product rich in intermediates HCFC-123 and/or HCFC-124, and respective intermediates are reacted with hydrogen fluoride in a second reactor as shown by the following formula 3 and/or formula 4, whereby a product containing the objective pentafluoroethane is obtained.

$CCl_2=CCl_2+3HF \rightarrow CF_3CHCl_2+2HCl$ (Formula 1)

$CCl_2=CCl_2+4HF \rightarrow CF_3CHClF+3HCl$ (Formula 2)

$CF_3CHCl_2+2HF \rightarrow CF_3CHF_2+2HCl$ (Formula 3)

$CF_3CHClF+HF \rightarrow CF_3CHF_2+HCl$ (Formula 4)

As for the production of 1,1,1,2-tetrafluoroethane, for example, a method of reacting hydrogen fluoride with trichloroethylene or 2-chloro-1,1,1-trifluoroethane (hereinafter sometimes referred to as "HCFC-133a") in the presence of a fluorination catalyst is known. Also, similarly to the above-described pentafluoroethane, a two-step method may be used. That is, a reaction of reacting trichloroethylene with hydrogen fluoride, shown by the following formula 5 is performed in a first reactor to produce an intermediate product rich in an intermediate HCFC-133a and subsequently, HCFC-133a is reacted with hydrogen fluoride in a second reactor as shown by formula 6, whereby a product containing objective 1,1,1,2-tetrafluoroethane is obtained.

$CCl_2=CHCl+3HF \rightarrow CF_3CH_2Cl+2HCl$ (Formula 5)

$CF_3CH_2Cl+HF \rightarrow CF_3CH_2F+HCl$ (Formula 6)

Furthermore, a method of producing two or more hydrofluorocarbons at the same time has been proposed. For example, WO95/15937 describes a method of reacting HCFC-133a with hydrogen fluoride to produce 1,1,1,2-tetrafluoroethane and reacting hydrogen fluoride with methylene chloride and trichloroethylene in the presence of the produced 1,1,1,2-tetrafluoroethane.

Japanese International Application Domestic Publication No. 7-507787 describes a method of reacting hydrogen fluoride, for example, with trichloroethylene to produce HCFC-133a, then reacting this HCFC-133a with hydrogen fluoride to produce 1,1,1,2-tetrafluoroethane, and during these steps, adding, for example, HCFC-123 and/or HCFC-124, thereby producing pentafluoroethane together with 1,1,1,2-tetrafluoroethane.

Also, Japanese Unexamined Patent Publication No. 8-27046 (JP-A-8-27046) describes a method of reacting hydrogen fluoride, for example, with HCFC-133a and HCFC-123 in a first rector, mixing the reaction product with tetrachloroethylene, feeding the mixture to a second reactor, and conducting a reaction under reaction conditions different from those in the first reactor, thereby obtaining a product containing 1,1,1,2-tetrafluoroethane and pentafluoroethane.

However, these methods have a problem particularly in simultaneously producing high-purity pentafluoroethane and 1,1,1,2-tetrafluoroethane in an economically advantageous manner using tetrachloroethylene and trichloroethylene which are general-purpose raw materials.

The reason therefor is that the reaction conditions in respective reactions shown by formulae 1 to 6 greatly differ from each other. To speak specifically on preferred reaction conditions in the production of pentafluoroethane, the steps shown by formulae 1 and 2 can be conducted under the conditions of, for example, a reaction pressure of 0.35 MPa, a reaction temperature of 310° C. and a hydrogen fluoride/tetrachloroethylene molar ratio of 10. Furthermore, the steps shown by formulae 3 and 4 can be conducted under the conditions of, for example, a reaction pressure of 0.4 MPa, a reaction temperature of 340° C. and a hydrogen fluoride/HCFC-123+HCFC-124 molar ratio of 8.

To speak specifically on preferred reaction conditions in the production of 1,1,1,2-tetrafluoroethane, the step shown by formula 5 can be conducted under the conditions of, for example, a reaction pressure of 0.35 MPa, a reaction temperature of 270° C. and a hydrogen fluoride/trichloroethylene molar ratio of 15. The step shown by formula 6 can be conducted under the conditions of, for example, a reaction pressure of 0.4 MPa, a reaction temperature of 340° C. and a hydrogen fluoride/HCFC-133a molar ratio of 6.

In particular, the optimal reaction temperature greatly differs between the steps of reacting hydrogen fluoride with respective starting materials of tetrachloroethylene and trichloroethylene and therefore, if a conventional method is used, this great difference in the reaction temperature brings out adverse effect of unreacted starting materials on the catalyst or causes increase of undesired impurities in some cases.

DISCLOSURE OF INVENTION

The present invention has been made under these circumstances and an object of the present invention is to provide a method for purifying tetrachloroethylene, which can remove a stabilizer contained in tetrachloroethylene, is easy in the operation and is industrially practicable, and a process for producing pentafluoroethane using the purification method.

It is another object of the present invention is to provide a process for producing two different high-purity hydrofluorocarbons which can be used as refrigerants, in an industrially advantageous manner.

As a result of extensive investigations to solve the above-described first object, the present inventors have found that when tetrachloroethylene containing a stabilizer is contacted with a zeolite having an average pore size of 3.4 to 11 Å and/or a carbonaceous adsorbent having an average pore size of 3.4 to 11 Å in a liquid phase, the amount of the stabilizer can be reduced. Furthermore, the present inventors have found that when the tetrachloroethylene reduced in a stabilizer is used as starting material, pentafluoroethane can be efficiently produced. The present invention has been accomplished based on these findings.

Thus, the present invention provides a method for purifying tetrachloroethylene, comprising contacting tetrachloroethylene containing, as a stabilizer, a hydroxyl group-containing aromatic compound with a zeolite having an average pore size of 3.4 to 11 Å and/or a carbonaceous adsorbent having an average pore size of 3.4 to 11 Å in a liquid phase to reduce the amount of the stabilizer.

The present invention also provides a process for producing tetrachloroethylene, reduced in a hydroxyl group-containing aromatic compound contained as a stabilizer, comprising using the purification method described above.

The present invention further provides a process for producing pentafluoroethane, comprising the following three steps:

(1) a step of reducing a hydroxyl group-containing aromatic compound contained in tetrachloroethylene by using the purification method described above;

(2) a step of reacting HF with the tetrachloroethylene reduced in the hydroxyl group-containing aromatic compound through the step (1), in the presence of an alumina-chromia catalyst in a gas phase to obtain a mixed gas containing 1,1-dichloro-2,2,2-trifluoroethane and 1-chloro-1,2,2,2-tetrafluoroethane; and (3) a step of reacting HF with the mixed gas containing 1,1-dichloro-2,2,2-trifluoroethane and 1-chloro-1,2,2,2-tetrafluoroethane obtained in the step (2), in the presence of an alumina-chromia catalyst, in a gas phase to obtain pentafluoroethane.

The present inventors have also found that the above-described second object can be attained by using a process comprising (A) a step of reacting hydrogen fluoride with a halogenated alkene and/or a halogenated alkane in the presence of a fluorination catalyst to produce a first hydrofluorocarbon; (B) a step of reacting hydrogen fluoride with a halogenated alkene and/or a halogenated alkane in the presence of a fluorination catalyst to produce a second hydrofluorocarbon; and (C) a step of joining and distilling the products obtained in the steps (A) and (B) to obtain the first hydrofluorocarbon and the second hydrofluorocarbon. The present invention has been accomplished based on this finding.

Thus, the present invention also provides a production process of a hydrofluorocarbon comprising (A) a step of reacting hydrogen fluoride with a halogenated alkene and/or a halogenated alkane in the presence of a fluorination catalyst to produce a first hydrofluorocarbon, (B) a step of reacting hydrogen fluoride with a halogenated alkene and/or a halogenated alkane in the presence of a fluorination catalyst to produce a second hydrofluorocarbon, and (C) a step of joining and then distilling the products obtained in the steps (A) and (B) to obtain the first hydrofluorocarbon and the second hydrofluorocarbon.

BEST MODE FOR CARRYING OUT THE INVENTION

The present invention will be described in detail below with respect to preferred embodiments.

The method for purifying tetrachloroethylene will be explained first.

The zeolite for use in the purification method of tetrachloroethylene according to the present invention suitably has an average pore size of 3.4 to 11 Å, preferably 3.4 to 10 Å. If the zeolite has an average pore size exceeding 11 Å, the amount of tetrachloroethylene adsorbed increases, whereas if the average pore size is less than 3.4 Å, the zeolite is reduced in the capability of adsorbing the stabilizer.

The zeolite preferably has an Si/Al ratio of 2 or less. If the Si/Al ratio of zeolite exceeds 2, the stabilizer is liable not to be selectively adsorbed. The zeolite is preferably at least one selected from the group consisting of molecular sieves 4A (MS-4A), molecular sieves 5A (MS-5A), molecular sieves 10×(MS-10×) and molecular sieves 13×(MS-13×). By using these zeolites, the water content in the tetrachloroethylene can also be reduced at the same time.

The carbonaceous adsorbent suitably has an average pore size of 3.4 to 11 Å. If the carbonaceous adsorbent has an average pore size exceeding 11 Å, the amount of tetrachloroethylene adsorbed increases, whereas if the average pore size is less than 3.4 Å, the carbonaceous adsorbent is reduced in the capability of adsorbing a stabilizer. The carbonaceous adsorbent is preferably molecular sieving carbon 4A and/or molecular sieving carbon 5A.

The zeolite and the carbonaceous adsorbent are preferably used individually in view of regeneration of the adsorbent, however, these may be used as a mixture. The ratio of zeolite and carbonaceous adsorbent mixed is not particularly limited, however, the zeolite is preferably mixed to a higher ratio because the water content in tetrachloroethylene can also be reduced.

For contacting tetrachloroethylene containing a stabilizer with the zeolite and/or the carbonaceous adsorbent in a liquid phase, a known method such as batch system and continuous system can be used. Industrially, a method of continuously passing the adsorbent in a fixed bed is preferred. The space velocity on a liquid basis (LHSV) can be appropriately selected according to the concentration of stabilizer and the amount of tetrachloroethylene treated, but usually, the space velocity is preferably from 1 to 50 hr$^{-1}$. Also, in order to industrially practice the method for reducing the stabilizer in tetrachloroethylene, a method of providing two adsorption towers and continuously conducting the purification by changing over these two towers may be used.

At the time of purifying tetrachloroethylene in a liquid phase, the treating temperature is preferably −20° C. to +80° C., more preferably from 0 to 50° C. If the treating temperature exceeds 80° C., the cost for equipment may increase in view of heating, pressure resistance and the like of the apparatus, whereas if the treating temperature is less than −20° C., cooling equipment or the like may be necessary. The pressure is preferably from 0 to 3 MPa, more preferably from 0 to 1 MPa. If the pressure exceeds 3 MPa, the profitability may decrease in view of pressure resistance requirements of the equipment.

As described above, the stabilizer contained in tetrachloroethylene can be reduced by using the purification method of the present invention. The purification method of the present invention is preferably used particularly for compounds having one or more hydroxyl groups in the benzene ring. Examples of compounds having one or more hydroxyl groups in the benzene ring include phenol, cresol, 2,6-di-t-butyl-p-cresol and aminomethylphenol.

When tetrachloroethylene containing a stabilizer is contacted with the zeolite and/or the carbonaceous adsorbent in a liquid phase under the above-described conditions, the tetrachloroethylene can be obtained where the amount of the stabilizer is reduced to 30 mass ppm or less. And, it is possible to obtain tetrachloroethylene which is reduced in the amount of the stabilizer to 10 mass ppm or less, further to 5 ppm or less.

Next, the process for producing pentafluoroethane will be explained.

The process for producing pentafluoroethane according to the present invention comprises the above-mentioned steps (1), (2) and (3).

The tetrachloroethylene obtained through the step (1) is preferably tetrachloroethylene reduced in the amount of the hydroxyl group-containing aromatic compound to 30 mass ppm or less, more preferably 10 mass ppm or less, still more preferably 5 mass ppm or less. When pentafluoroethane is produced starting from tetrachloroethylene reduced in the hydroxyl group-containing aromatic compound to 30 mass ppm or less, the catalyst used in the production process can have a long life and the pentafluoroethane can be produced efficiently and profitably.

The production process of pentafluoroethane of the present invention can be represented by the following reaction formulae:

$$CCl_2=CCl_2+3HF \rightarrow CF_3CHCl_2+2HCl \quad \text{(Formula 1)}$$

$$CCl_2=CCl_2+4HF \rightarrow CF_3CHClF+3HCl \quad \text{(Formula 2)}$$

$$CF_3CHCl_2+2HF \rightarrow CF_3CHF_2+2HCl \quad \text{(Formula 3)}$$

$$CF_3CHClF+HF \rightarrow CF_3CHF_2+HCl \quad \text{(Formula 4)}$$

These reactions are conducted in a gas phase in the presence of an alumina-chromia catalyst, however, the reaction conditions differ among the reactions. For example, the first reaction shown by formulae 1 and 2 can be conducted under the conditions of a reaction pressure of about 0.3 MPa, a reaction temperature of about 300° C. and HF/PCE of 6 (molar ratio), and the second reaction shown by formulae 3 and 4 can be conducted under the conditions of a reaction pressure of about 0.4 MPa, a reaction temperature of about 330° C. and HF/(CF$_3$CHCl$_2$+CF$_3$CHClF) of 4 to 8 (molar ratio).

Next, the production process of a hydrofluorocarbon will be explained.

The process for producing a hydrofluorocarbon according to the present invention comprises (A) a step of reacting hydrogen fluoride with a halogenated alkene and/or a halogenated alkane in the presence of a fluorination catalyst to produce a first hydrofluorocarbon, (B) a step of reacting hydrogen fluoride with a halogenated alkene and/or a halogenated alkane in the presence of a fluorination catalyst to produce a second hydrofluorocarbon, and (C) a step of joining and then distilling the products obtained in the steps (A) and (B) to obtain the first hydrofluorocarbon and the second hydrofluorocarbon.

Examples of the hydrofluorocarbon which can be produced by using the process include difluoromethane, trifluoromethane, 1,2-difluoroethane, 1,1,1-trifluoroethane, 1,1,1,2-tetrafluoroethane and pentafluoroethane.

Examples of the halogenated alkene which can be used as a starting material include chloroethylene, 1,1-dichloroethylene, trichloroethylene, trifluoroethylene, tetra-chloroethylene, tetrafluoroethylene and chlorotrifluoroethylene. Examples of the halogenated alkane include dichloromethane, chlorofluoromethane, trichloromethane, chlorodifluoromethane, 2-chloro-1,1,1-trifluoroethane, 2,2-dichloro-1,1,1-trifluoroethane and 2-chloro-1,1,1,2-tetrafluoroethane.

For example, in the case of producing pentafluoroethane as the first hydrofluorocarbon, the step (A) is preferably to react hydrogen fluoride with at least one member selected from the group consisting of tetrachloroethylene, 2,2-dichloro-1,1,1-trifluoroethane and 2-chloro-1,1,1,2-tetrafluoroethane in the presence of a fluorination catalyst.

The step (A) preferably comprises a step (1) of reacting hydrogen fluoride with tetrachloroethylene in a presence of a fluorination catalyst in a first reaction zone to produce a gas containing 2,2-dichloro-1,1,1-trifluoroethane and/or 2-chloro-1,1,1,2-tetrafluoroethane, and a step (2) of reacting hydrogen fluoride with a gas containing 2,2-dichloro-1,1,1-trifluoroethane and/or 2-chloro-1,1,1,2-tetrafluoroethane in the presence of a fluorination catalyst in a second reaction zone to produce a gas containing pentafluoroethane.

For example, in the case of producing pentafluoroethane as the first hydrofluorocarbon and 1,1,1,2-tetrafluoroethane as the second hydrofluorocarbon, in addition to the above-described step (A), the step (B) is preferably to react hydrogen fluoride with trichloroethylene and/or 2-chloro-1,1,1-trifluoroethane in the presence of a fluorination catalyst to produce 1,1,1,2-tetrafluoroethane as the second hydrofluorocarbon.

The step (B) preferably comprises a step (3) of reacting hydrogen fluoride with trichloroethylene in a presence of a fluorination catalyst in a third reaction zone to produce a gas containing 2-chloro-1,1,1-trifluoroethane, and a step (4) of reacting hydrogen fluoride with a gas containing 2-chloro-1,1,1-trifluoroethane in the presence of a fluorination catalyst in a fourth reaction zone to produce a gas containing 1,1,1,2-tetrafluoroethane.

The step (C) is preferably to join and then distill the gas containing pentafluoroethane obtained in the step (A) and the gas containing 1,1,1,2-tetrafluoroethane obtained in the step (B).

In the case of producing pentafluoroethane as the first hydrofluorocarbon and 1,1,1,2-tetrafluoroethane as the second hydrofluorocarbon, preferably, the step (A) comprises a step (1) of reacting hydrogen fluoride with tetrachloroethylene in the presence of a fluorination catalyst in a first reaction zone to obtain a gas containing hydrogen chloride, 2,2-dichloro-1,1,1-trifluoroethane, 2-chloro-1,1,1,2-tetrafluoroethane, pentafluoroethane and/or hydrogen fluoride and a step (2) of reacting hydrogen fluoride with a gas containing 2,2-dichloro-1,1,1-trifluoroethane and/or 2-chloro-1,1,1,2-tetrafluoroethane in the presence of a fluorination catalyst in a second reaction zone to obtain a gas containing hydrogen chloride, pentafluoroethane, 2,2-dichloro-1,1,1-trifluoroethane, 2-chloro-1,1,1,2-tetrafluoroethane and/or hydrogen fluoride, the step (B) comprises a step (3) of reacting hydrogen fluoride with trichloroethylene in the presence of a fluorination catalyst in a third reaction zone to obtain a gas containing hydrogen chloride, 2-chloro-1,1,1-trifluoroethane and/or hydrogen fluoride and a step (4) of reacting hydrogen fluoride with a gas containing 2-chloro-1,1,1-trifluoroethane in the presence of a fluorination catalyst in a fourth reaction zone to obtain a gas containing hydrogen chloride, 1,1,1,2-tetrafluoroethane, 2-chloro-1,1,1-trifluoroethane and/or hydrogen fluoride, and the step (C) comprises a step (5) of joining the gases obtained in said steps (1) to (4), introducing the joined gas into a distillation tower, and then distilling the gas to obtain pentafluoroethane and 1,1,1,2-tetrafluoroethane.

In this process, for example, the two reaction steps for producing pentafluoroethane from tetrachloroethylene and hydrogen fluoride and the two reaction steps for producing 1,1,1,2-tetrafluoroethane from trichloroethylene and hydrogen fluoride are conducted separately, so that the reaction conditions can be efficiently controlled and, thereby, the problems such as effect on the catalyst activity and increase of impurities can be avoided. The products in these four reaction steps are joined and introduced into one distillation tower, whereby high-purity pentafluoroethane and 1,1,1,2-tetrafluoroethane can be produced with good efficiency using a simple apparatus.

In all of the first to fourth reaction zones, the reaction pressure is preferably from atmospheric pressure to 0.9 MPa. Furthermore, it is preferred that the pressure in the second reaction zone is higher than the pressure in the first reaction zone and the pressure in the fourth reaction zone is higher than the pressure in the third reaction zone.

The fluorination catalyst for use in this process may be a conventionally known fluorination catalyst. In this process, an optimal catalyst can be selected for each of the steps of producing two different compounds. However, the fluorination catalyst is preferably a supported or bulk catalyst mainly comprising a trivalent chromium oxide.

In this process, after gases containing two different hydrofluorocarbons are obtained in respective steps, these product gases are joined and introduced into a distillation tower. For example, the gases obtained in the steps (1) to (4) are preferably joined and introduced into a first distillation tower to separate hydrogen chloride, 2-chloro-1,1,1-trifluoroethane, 2-chloro-1,1,1,2-tetrafluoroethane, pentafluoroethane and/or 1,1,1,2-tetrafluoroethane from the top and separate hydrogen fluoride, 2,2-dichloro-1,1,1-trifluoroethane and/or 2-chloro-1,1,1-trifluoroethane from the bottom.

The hydrogen fluoride, 2,2-dichloro-1,1,1-trifluoroethane and/or 2-chloro-1,1,1-trifluoroethane separated from the bottom of the first distillation tower are preferably circulated to the reaction step. Also, the hydrogen fluoride, 2,2-dichloro-1,1,1-trifluoroethane and/or 2-chloro-1,1,1-trifluoroethane separated from the bottom of the first distillation tower are preferably introduced into a second distillation tower and after purification by separation, circulated to the reaction step.

The hydrogen fluoride separated in the second distillation tower is preferably circulated to at least one reaction zone of the first to fourth reaction zones. The gas containing 2,2-dichloro-1,1,1-trifluoroethane, separated in the second distillation tower is preferably circulated to the second reaction zone and the gas containing 2-chloro-1,1,1-trifluoroethane, separated in the second distillation tower is preferably circulated to the fourth reaction zone.

The hydrogen chloride, 2-chloro-1,1,1-trifluoroethane, 2-chloro-1,1,1,2-tetrafluoroethane, pentafluoroethane and/or 1,1,1,2-tetrafluoroethane, separated from the top of the first distillation tower are preferably introduced into a third distillation tower to obtain pentafluoroethane and 1,1,1,2-tetrafluoroethane from the top. The gas obtained from the top of the third distillation tower is preferably rich in 1,1,1,2-tetrafluoroethane. In this process, the pressure inside the respective towers is preferably from atmospheric pressure to 3 MPa.

Alternativly, the process for producing a hydrofluorocarbon according to the present invention, preferably, comprises (A) a step of reacting hydrogen fluoride with at least one member selected from the group consisting of tetrachloroethylene, 2,2-dichloro-1,1,1-trifluoroethane and 2-chloro-1,1,1,2-tetrafluoroethane in the presence of a fluorination catalyst to produce pentafluoroethane, (B) a step of reacting hydrogen fluoride with trichloroethylene and/or 2-chloro-1,1,1-trifluoroethane in the presence of a fluorination catalyst to produce 1,1,1,2-tetrafluoroethane, and (C) a step of joining the products obtained in the steps (A) and (B), introducing these products into a distillation tower, separating a gas mainly containing hydrogen chloride from the top, separating a gas containing pentafluoroethane and 1,1,1,2-tetrafluoroethane from the bottom, and distilling the gas obtained from the bottom to obtain pentafluoroethane and 1,1,1,2-tetrafluoroethane.

The step (A) preferably comprises a step (1) of reacting hydrogen fluoride with tetrachloroethylene in the presence of a fluorination catalyst in a first reaction zone to produce a gas containing 2,2-dichloro-1,1,1-trifluoroethane and/or 2-chloro-1,1,1,2-tetrafluoroethane, and a step (2) of reacting hydrogen fluoride with a gas containing 2,2-dichloro-1,1,1-trifluoroethane and/or 2-chloro-1,1,1,2-tetrafluoroethane in the presence of a fluorination catalyst in a second reaction zone to produce a gas containing pentafluoroethane.

The step (B) preferably comprises a step (3) of reacting hydrogen fluoride with trichloroethylene in the presence of a fluorination catalyst in a third reaction zone to produce a gas containing 2-chloro-1,1,1-trifluoroethane, and a step (4) of reacting hydrogen fluoride with a gas containing 2-chloro-1,1,1-trifluoroethane in the presence of a fluorination catalyst in a fourth reaction zone to produce a gas containing 1,1,1,2-tetrafluoroethane.

Furthermore, in this process, preferably, the step (A) comprises a step (1) of reacting hydrogen fluoride with tetrachloroethylene in the presence of a fluorination catalyst in a gas phase in a first reaction zone to produce a gas containing hydrogen chloride, 2,2-dichloro-1,1,1-trifluoroethane, 2-chloro-1,1,1,2-tetrafluoroethane, pentafluoroethane and hydrogen fluoride and a step (2) of reacting hydrogen fluoride with a gas containing 2,2-dichloro-1,1,1-trifluoroethane and/or 2-chloro-1,1,1,2-tetrafluoroethane in the presence of a fluorination catalyst in a gas phase in a second reaction zone to produce a gas containing hydrogen chloride, pentafluoroethane, 2,2-dichloro-1,1,1-trifluoroethane, 2-chloro-1,1,1,2-tetrafluoroethane and hydrogen fluoride, the step (B) comprises a step (3) of reacting hydrogen fluoride with trichloroethylene in the presence of a fluorination catalyst in a gas phase in a third reaction zone to produce a gas containing hydrogen chloride, 2-chloro-1,1,1-trifluoroethane and hydrogen fluoride and a step (4) of reacting hydrogen fluoride with a gas containing 2-chloro-1,1,1-trifluoroethane in the presence of a fluorination catalyst in a gas phase in a fourth reaction zone to produce a gas containing hydrogen chloride, 1,1,1,2-tetrafluoroethane, 2-chloro-1,1,1-trifluoroethane and hydrogen fluoride, and the step (C) comprises a step (5) of joining the gases obtained in the steps (1) to (4), introducing these gases into a distillation tower, separating a gas mainly containing hydrogen chloride from the top, separating a gas containing pentafluoroethane and 1,1,1,2-tetrafluoroethane from the bottom, and distilling the gas obtained from the bottom to obtain pentafluoroethane and 1,1,1,2-tetrafluoroethane.

In this process, the two reaction steps for producing pentafluoroethane from tetrachloroethylene and hydrogen fluoride the two reaction steps for producing 1,1,1,2-tetrafluoroethane from trichloroethylene and hydrogen fluoride are conducted separately, so that the reaction conditions can be effectively controlled and thereby, the effect on catalyst activity, increase of impurities and the like can be avoided. Then, the products in these four steps are joined and introduced into one distillation tower, whereby high-purity pentafluoroethane and 1,1,1,2-tetrafluoroethane can be produced with good efficiency by a simple apparatus.

In all of the first to fourth reaction zones, the reaction pressure is preferably from atmospheric pressure to 0.9 MPa. Furthermore, it is preferred that the pressure in the second reaction zone is higher than the pressure in the first reaction zone and the pressure in the fourth reaction zone is higher than the pressure in the third reaction zone.

The fluorination catalyst for use in this process may be a conventionally known fluorination catalyst. In this process, an optimal catalyst can be selected for each of the steps of producing pentafluoroethane and 1,1,1,2-tetrafluoroethane, however, the fluorination catalyst is preferably a supported or bulk catalyst mainly comprising a trivalent chromium oxide.

In this process, after gases containing pentafluoroethane and 1,1,1,2-tetrafluoroethane are obtained in respective steps, these product gases are joined and introduced into a distillation tower. For example, the gases obtained in the steps (1) to (4) are preferably joined and introduced into a first distillation tower to separate hydrogen chloride from the top and separate a gas mainly containing 2-chloro-1,1,1-trifluoroethane, 2,2-dichloro-1,1,1-trifluoroethane, 2-chloro-1,1,1,2-tetrafluoroethane, pentafluoroethane, 1,1,1,2-tetrafluoroethane and/or hydrogen fluoride from the bottom.

The gas mainly containing 2-chloro-1,1,1-trifluoroethane, 2,2-dichloro-1,1,1-trifluoroethane, 2-chloro-1,1,1,2-tetrafluoroethane, pentafluoroethane, 1,1,1,2-tetrafluoroethane and/or hydrogen fluoride, separated from the bottom of the first distillation tower is preferably introduced in a second distillation tower. In the second distillation tower, pentafluoroethane, 1,1,1,2-tetrafluoroethane and/or 2-chloro-1,1,1,2-tetrafluoroethane are separated from the top and 2-chloro-1,1,1-trifluoroethane, 2,2-dichloro-1,1,1-trifluoroethane and/or hydrogen fluoride are preferably separated from the bottom. The gas separated from the top of the second distillation tower is preferably rich in 1,1,1,2-tetrafluoroethane.

It is preferred that the gas mainly containing 2-chloro-1,1,1-trifluoroethane, 2,2-dichloro-1,1,1-trifluoroethane and/or hydrogen fluoride, separated from the bottom of the second distillation tower is introduced into a third distillation tower to separate and purify respective components and the components are circulated to the reaction step. Furthermore, hydrogen fluoride separated in the third distillation tower is preferably circulated to at least one reaction zone of the first to fourth reaction zones.

The gas mainly containing 2,2-dichloro-1,1,1-tri-fluoroethane, separated in the third distillation tower is preferably circulated to the second reaction zone.

The gas mainly containing 2-chloro-1,1,1-trifluoroethane, separated in the third distillation tower is preferably circulated to the fourth reaction zone.

It is preferred that the gas containing pentafluoro-ethane, 1,1,1,2-tetrafluoroethane and/or 2-chloro-1,1,1,2-tetrafluoroethane, separated from the top of the second distillation tower is introduced into a fourth distillation tower to separate pentafluoroethane and 1,1,1,2-tetrafluoroethane from the top and separate 2-chloro-1,1,1,2-tetrafluoroethane from the bottom, and 2-chloro-1,1,1,2-tetrafluoroethane is circulated to the second reaction zone. In this process, the pressure inside the respective towers is preferably from atmospheric pressure to 3 MPa.

In the production process of a hydrofluorocarbon according to the present invention, unreacted starting materials and intermediates in respective reaction steps can be separated by distillation and circulated to each reaction step and therefore, the yield of the objective compound can be increased.

In the production process of a hydrofluorocarbon according to the present invention, two different hydrofluorocarbons are produced from hydrogen fluoride and two or more starting compounds and in order to overcome the difference in the optimal catalyst compositions and optimal reaction conditions for the respective hydrofluorocarbons produced, the reactions are performed by connecting in parallel two or more reactors of using solid catalysts different from each other or performing the reactions at temperatures different from each other, and supplying appropriate reaction starting materials to each reactor.

The present invention will further be illustrated below by referring to Examples and Comparative Examples, however, the present invention is not limited to any extent by these examples.

STARTING MATERIAL EXAMPLE

A commercially available tetrachloroethylene was analyzed by a gas chromatograph (column: capillary system/FID method), as a result, the total amount of phenol and cresol contained as stabilizers was 150 mass ppm and the water content in the tetrachloroethylene was about 50 mass ppm.

Example 1

Into a stainless steel cylinder having a volume of 200 ml, 20 g of zeolite [molecular sieves 5A (produced by Union Showa K.K., average pore size: 4.2 Å, Si/Al ratio=1)] was filled. After vacuum drying the zeolite, 100 g of tetrachloroethylene described in the Starting Material Example was filled while cooling the cylinder and the contents were occasionally stirred while keeping the temperature at 20° C. After about 4 hours, a part of the liquid phase moiety was sampled and analyzed under the gas chromatograph conditions as mentioned in the Starting Material Example. As a result, both phenol and cresol as stabilizers were not detected. Also, the water content in tetrachloroethylene after the treatment was analyzed using Karl Fischer's method and found to be 3 mass ppm or less.

Example 2

Into a stainless steel cylinder having a content volume of 200 ml, 20 g of carbonaceous adsorbent [molecular sieving carbon 5A, produced by Takeda Chemical Industries, Ltd., average pore size: 5 Å] was filled. After vacuum drying the carbonaceous adsorbent, 80 g of tetrachloroethylene described in the Starting Material Example was filled while cooling the cylinder and the contents were occasionally stirred while keeping the temperature at 20° C. After about 5 hours, a part of the liquid phase moiety was sampled and analyzed under the gas chromatograph conditions as mentioned in the Starting Material Example. As a result, both phenol and cresol as stabilizers were not detected.

Example 3

A treatment and an analysis were conducted by the same procedures and under the same conditions as in Example 1 except that 20 g of zeolite [molecular sieves 13×(produced by Union Showa K.K., average pore size: 10 Å, Si/Al ratio=0.81)] was filled as the adsorbent. As a result, both phenol and cresol were not detected.

Comparative Example 1

A treatment and an analysis were conducted by the same procedures and under the same conditions as in Example 1 except that 20 g of zeolite [molecular sieves XH-9 (produced by Union Showa K.K., average pore size: 3.2 Å, Si/Al ratio=1)] was filled as the adsorbent. As a result, phenol and cresol as stabilizers were scarcely adsorbed and the total amount thereof was 132 mass ppm. This reveals that when a zeolite having an average pore size of less than 3.4 Å is used, the efficiency in the adsorption of a stabilizer is low.

Comparative Example 2

A treatment and an analysis were conducted by the same procedures and under the same conditions as in Example 2 except that 20 g of carbonaceous adsorbent [activated carbon, Granular Shirosagi KL, produced by Takeda Chemical Industries, Ltd., average pore size: 35 Å] was filled as the adsorbent. As a result, phenol and cresol as stabilizers were scarcely adsorbed and the total amount thereof was 119 mass ppm. A large heat of adsorption was generated due to the adsorption of tetrachloroethylene and new decomposition products were detected.

Example 4

Into a stainless steel cylinder having a volume of 200 ml, a mixture containing 15 g of molecular sieves 5A described in Example 1 and 5 g of molecular sieving carbon 5A described in Example 2 was filled. After vacuum drying the adsorbent, 80 g of tetrachloroethylene described in the Starting Material Example was filled while cooling the cylinder and the contents were occasionally stirred while keeping the temperature at 20° C. After about 4 hours, a part of the liquid phase moiety was sampled and analyzed under the gas chromatograph conditions as mentioned in the Starting Material Example. As a result, both phenol and cresol as stabilizers were not detected. Also, the water content in tetrachloroethylene was analyzed and found to be 5 mass ppm or less.

Example 5

Into a stainless steel cylinder having a volume of 5 liter, 4.8 liter of molecular sieves 5A (MS-5A) was filled and tetrachloroethylene described in the Starting Material Example was continuously supplied at a linear velocity of 10 liter/hr$^{-1}$ in a liquid phase under the conditions of room temperature (15° C.) and a pressure of about 0.3 MPa. After 100 hours, 300 hours and 500 hours from the initiation of supply, the outlet liquid was sampled and analyzed. As a result, in any sample, phenol and cresol as stabilizers were not detected. Also, in any sample, the water content was 5 mass ppm or less.

Then, an alumina-chromia catalyst was filled in a reactor and a continuous reaction was conducted starting from the tetrachloroethylene obtained above and HF under the conditions of a reaction temperature of 300° C., a reaction pressure of about 0.3 MPa, HF/PCE of 6 (molar ratio) and SV of 750 hr$^{-1}$.

After 24 hours from the initiation of reaction, the PCE conversion was 99.6%, and after 500 hours, the PCE conversion was 99.4%. Thus, no reduction of the activity of catalyst was confirmed.

Comparative Example 3

An alumina-chromia catalyst was filled in a reactor and a continuous reaction was conducted starting from tetrachloroethylene containing stabilizers (total amount: 150 mass ppm) as mentioned in the Starting Material Example and HF under the conditions of a reaction temperature of 300° C., a reaction pressure of about 0.3 MPa, HF/PCE of 6 (molar ratio) and SV of 750 hr$^{-1}$.

After 24 hours from the initiation of reaction, the PCE conversion was 99.5%, and after 500 hours, the PCE conversion was 81.2%. Thus, reduction of the activity of catalyst was confirmed. From this, it is apparent that the stabilizer has relation to the reduction of activity of catalyst.

Example 6

Figure 1:
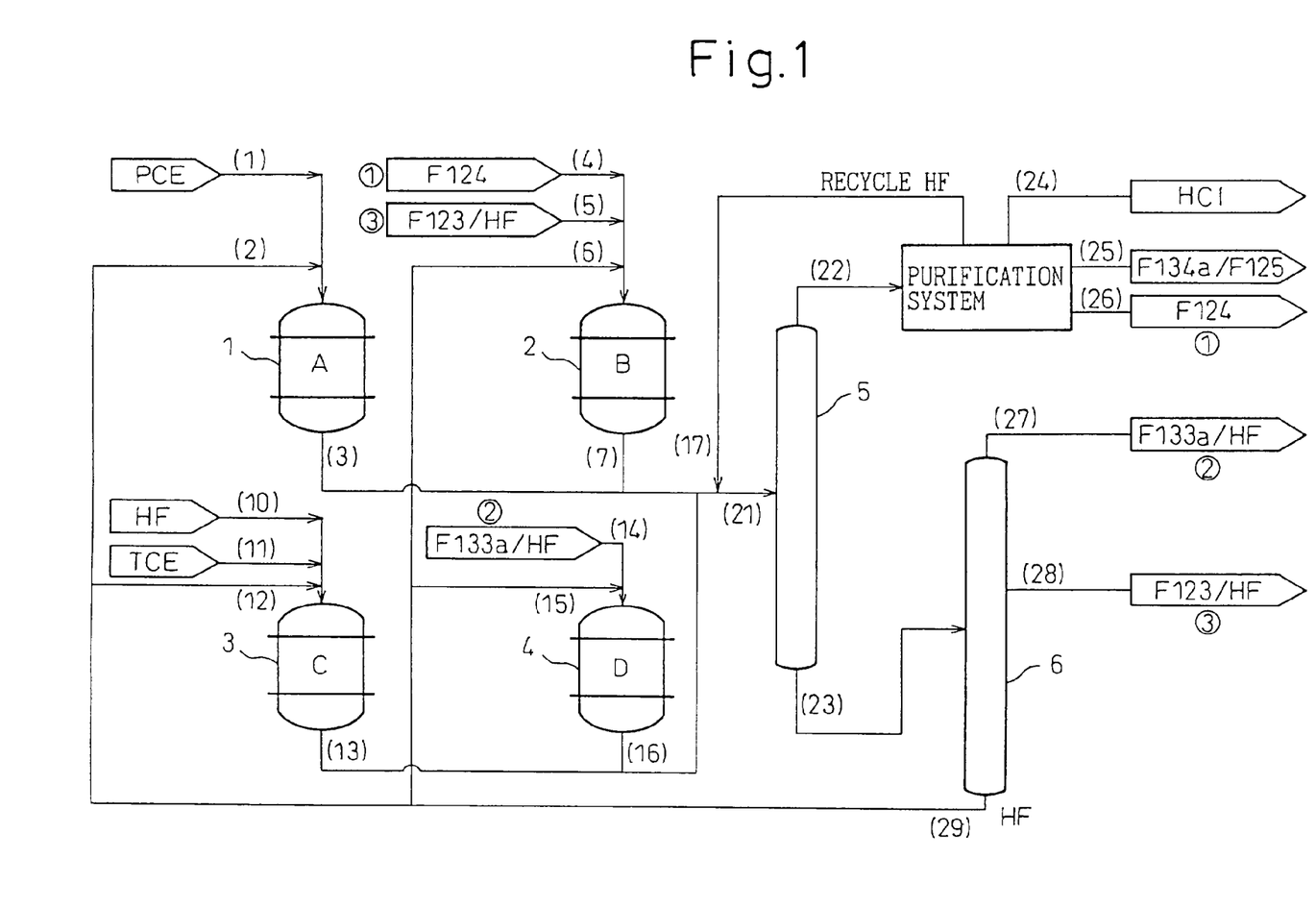
FIG. 1 is a schematic view of an apparatus for carrying out the process for producing a hydrofluorocarbon according to the present invention.

Using the apparatus shown in FIG. 1, the following procedures were conducted. In FIG. 1, the compounds are shown as follows.

Tetrachloroethylene: PCE
Trichloroethylene: TCE
2,2-Dichloro-1,1,1-trifluoroethane: F123
2-Chloro-1,1,1,2-tetrafluoroethane: F124
2-Chloro-1,1,1-trifluoroethane: F133a
Pentafluoroethane: F125
1,1,1,2-Tetrafluoroethane: F134a
Hydrogen fluoride: HF
Hydrogen chloride: HCl The apparatus shown in FIG. 1 is basically constructed by four gas phase reactors A, B, C and D capable of holding catalysts different from each other, a first distillation tower, a purification system for purifying a gas containing pentafluoroethane and 1,1,1,2-tetrafluoroethane separated from the top of the first distillation tower, and a second distillation tower for separating and purifying intermediate compounds such as HCFC-123 and unreacted hydrogen fluoride separated from the bottom of the first distillation tower.

In FIG. 1, reactions for producing pentafluoroethane are performed in reactors A and B. First, starting material tetrachloroethylene (PCE) (1) is introduced into the reactor A. In the reactor A, a catalyst optimal for the reaction is filled. Simultaneously, hydrogen fluoride (29) separated in the second distillation tower is introduced as (2) into the reactor A. Hydrogen fluoride can be newly added and introduced, if desired. In the reactor A, reactions shown by the hereinbefore-mentioned formulae 1 and 2 take place and reactions shown by the hereinbefore-mentioned formulae 3 and 4 partially take place, whereby a first product (3) containing HCl and intermediates HCFC-123, HCFC-124 and HFC-125 is produced. The first product (3) is joined with a second product (7), a third product (13) and a fourth product (16) which are described later, and introduced as (21) into a first distillation tower.

Into the reactor B, HCFC-124 (26) separated in the purification system is introduced as (4) (in FIG. 1, ① shows that (26) and (4) are connected, ② shows that (27) and (14) are connected, and ③ shows that (28) and (5) are connected), HCFC-123/HF (28) separated in the second distillation tower is introduced as (5), and a part of hydrogen fluoride (HF) (29) separated from the bottom of the second distillation tower is circulated and introduced as (6). The reactor B is also filled with a catalyst optimal for the reaction. In the reactor B, reactions shown by the hereinbefore-mentioned formulae 3 and 4 take place and a second product (7) containing HCl, objective HFC-125 and unreacted HCFC-123 and HCFC-124 is produced. The second product (7) is joined with gases from other reactors and introduced as (21) into the first distillation tower.

On the other hand, reactions for producing 1,1,1,2-tetrafluoroethane are performed in reactors C and D. Into the reactor C, starting material trichloroethylene (TCE) (11) is introduced, and newly added hydrogen fluoride (10) and circulated hydrogen fluoride (12) are introduced. In the reactor C, a reaction shown by the hereinbefore-mentioned formula 5 mainly takes place to produce a third product (13) containing HCl and intermediate HCFC-133a and the third product (13) is joined with gases from other reactors and introduced as (21) into the first distillation tower.

Into the reactor D, HCFC-133a/HF (27) separated in the second distillation tower and circulated hydrogen fluoride (15) are introduced and a reaction shown by the hereinbefore-mentioned formula 6 mainly takes place to produce a fourth product (16) containing HCl, objective HFC-134a and unreacted HCFC-133a and the fourth product (16) is joined with gases from other reactors and introduced as (21) into the first distillation tower.

The first product (3), the second product (7), the third product (13) and the fourth product (16) are joined and the joined product (21) is introduced into the first distillation tower. From the top of the first distillation tower, a first top fraction (22) mainly comprising HCl, HFC-134a, HFC-125, HCFC-124, HCFC-133a and hydrogen fluoride is eluted. This first top fraction is supplied to the purification system and separated into HCl (24), HFC-134a/HFC-125 (25), HCFC-124 (26), recycle HF (17) and the like. The purification system contains a third distillation tower (not shown). HCFC-124 and hydrogen fluoride each is circulated to each reaction step and reused, and HCl, HFC-134a and HFC-125 are recovered as products.

From the bottom of the first distillation tower, a first bottom fraction (23) mainly comprising hydrogen fluoride, HCFC-123 and HCFC-133a is eluted. This first bottom fraction (23) is introduced into the second distillation tower and HCFC-133a/HF (27) are recovered from the top and circulated to the reactor D. HCFC-123/HF (28) are drawn out from the side-cut plate provided upper than the feed plate of the second distillation tower, and circulated to the reactor B. From the bottom of the second distillation tower, HF (29) is recovered and this is circulated to each of the reactors A, B, C and D according to the necessity.

An example of the operation according to the above-described method is described below by referring to the apparatus shown in FIG. 1.

Assuming that the flow rate of the joined product (21) is 100 (kg/hr), the mass ratio (mass %) of each component in process lines (1) to (7), (10) to (17), and (21) to (29) is shown in Tables 1 and 2.

TABLE 1

|  | (1) | (2) | (3) | (4) | (5) | (6) | (7) | (10) | (11) | (12) | (13) | (14) | (15) | (16) | (17) |
|---|---|---|---|---|---|---|---|---|---|---|---|---|---|---|---|
| HFC-125 (F125) | 0.00 | 0.00 | 0.35 | 0.00 | 0.00 | 0.00 | 1.35 | 0.00 | 0.00 | 0.00 | 0.00 | 0.00 | 0.00 | 0.01 | 0.00 |
| HCFC-124 (F124) | 0.00 | 0.00 | 0.97 | 5.10 | 0.00 | 0.00 | 4.10 | 0.00 | 0.00 | 0.00 | 0.01 | 0.01 | 0.00 | 0.04 | 0.26 |
| HCFC-123 (F123) | 0.00 | 0.01 | 0.65 | 0.00 | 0.80 | 0.00 | 0.23 | 0.00 | 0.00 | 0.02 | 0.01 | 0.01 | 0.07 | 0.03 | 0.00 |
| HFC-134a (F134a) | 0.00 | 0.00 | 0.00 | 0.03 | 0.00 | 0.00 | 0.06 | 0.00 | 0.00 | 0.00 | 0.05 | 0.00 | 0.00 | 3.07 | 0.01 |
| HCFC-133a (F133a) | 0.00 | 0.00 | 0.00 | 0.31 | 0.00 | 0.00 | 0.28 | 0.00 | 0.00 | 0.00 | 3.57 | 29.85 | 0.00 | 26.27 | 0.05 |
| HF | 0.00 | 4.57 | 3.38 | 0.45 | 4.64 | 1.35 | 6.14 | 3.97 | 0.00 | 5.20 | 7.32 | 3.61 | 32.24 | 35.23 | 0.13 |
| HCl | 0.00 | 0.00 | 1.61 | 0.00 | 0.00 | 0.00 | 0.56 | 0.00 | 0.00 | 0.00 | 2.25 | 0.00 | 0.00 | 1.13 | 0.00 |
| PCE | 2.53 | 0.00 | 0.00 | 0.00 | 0.00 | 0.00 | 0.00 | 0.00 | 0.00 | 0.00 | 0.00 | 0.00 | 0.00 | 0.00 | 0.00 |
| TCE | 0.00 | 0.00 | 0.00 | 0.00 | 0.00 | 0.00 | 0.00 | 0.00 | 4.02 | 0.00 | 0.00 | 0.00 | 0.00 | 0.00 | 0.00 |
| Others | 0.00 | 0.00 | 0.15 | 0.06 | 0.00 | 0.00 | 0.04 | 0.00 | 0.00 | 0.02 | 0.03 | 0.65 | 0.00 | 0.65 | 0.00 |
| Total | 2.53 | 4.58 | 7.11 | 5.96 | 5.45 | 1.35 | 12.76 | 3.97 | 4.02 | 5.25 | 13.25 | 34.12 | 32.31 | 66.43 | 0.45 |

TABLE 2

|  | (21) | (22) | (23) | (24) | (25) | (26) | (27) | (28) | (29) |
|---|---|---|---|---|---|---|---|---|---|
| HFC-125 (F125) | 1.72 | 1.72 | 0.00 | 0.33 | 1.39 | 0.00 | 0.00 | 0.00 | 0.00 |
| HCFC-124 (F124) | 5.38 | 5.37 | 0.01 | 0.00 | 0.27 | 5.10 | 0.01 | 0.00 | 0.00 |
| HCFC-123 (F123) | 0.91 | 0.00 | 0.91 | 0.00 | 0.00 | 0.00 | 0.01 | 0.80 | 0.10 |
| HFC-134a (F134a) | 3.20 | 3.19 | 0.00 | 0.00 | 3.16 | 0.03 | 0.00 | 0.00 | 0.00 |
| HCFC-133a (F133a) | 30.16 | 0.31 | 29.85 | 0.00 | 0.00 | 0.31 | 29.85 | 0.00 | 0.00 |
| HF | 52.21 | 0.60 | 51.61 | 0.00 | 0.15 | 0.45 | 3.61 | 4.64 | 43.35 |
| HCl | 5.55 | 5.55 | 0.00 | 5.55 | 0.00 | 0.00 | 0.00 | 0.00 | 0.00 |
| PCE | 0.00 | 0.00 | 0.00 | 0.00 | 0.00 | 0.00 | 0.00 | 0.00 | 0.00 |
| TCE | 0.00 | 0.00 | 0.00 | 0.00 | 0.00 | 0.00 | 0.00 | 0.00 | 0.00 |
| Others | 0.86 | 0.14 | 0.72 | 0.00 | 0.08 | 0.06 | 0.65 | 0.00 | 0.03 |
| Total | 100.00 | 16.89 | 83.11 | 5.88 | 5.05 | 5.96 | 34.12 | 5.45 | 43.49 |

Example 7

Figure 2:
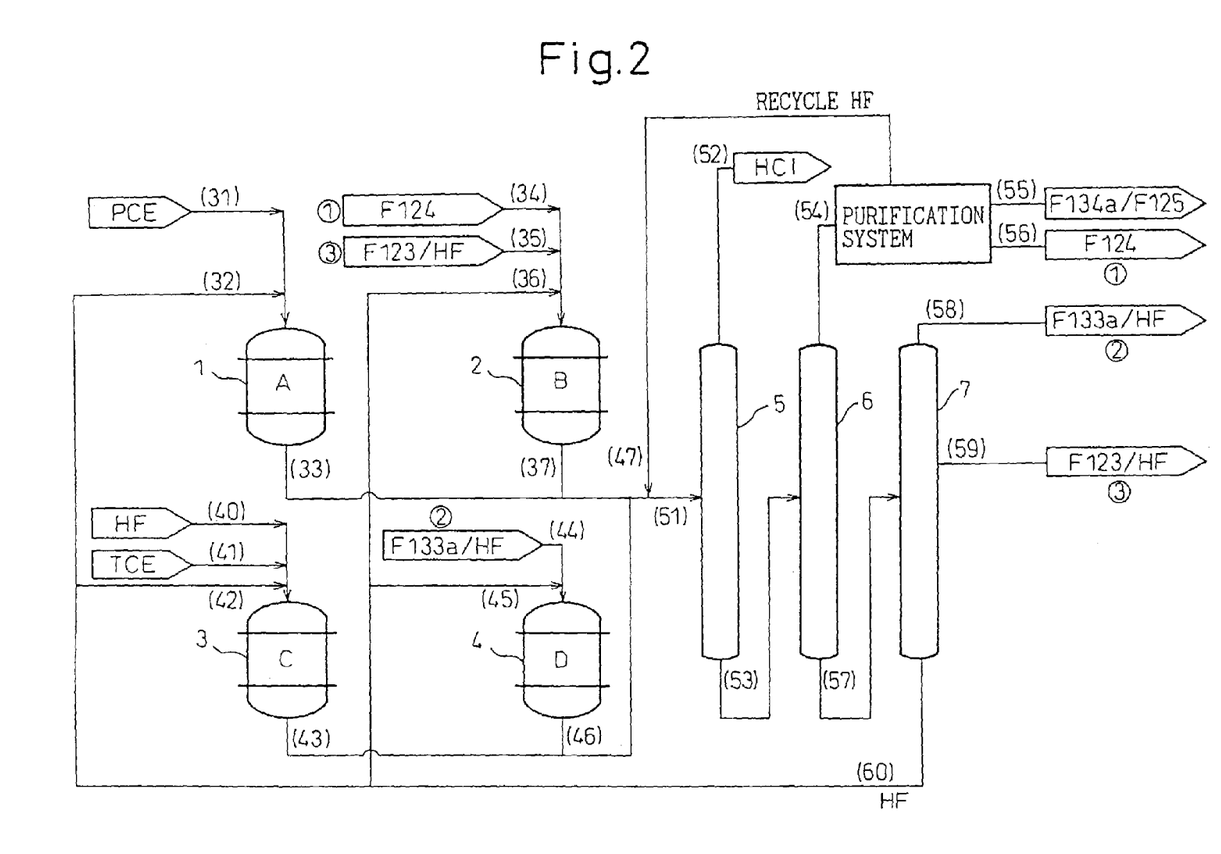
FIG. 2 is a schematic view of another apparatus for carrying out the process for producing a hydrofluorocarbon according to the present invention.

Using the apparatus shown in FIG. 2, the following procedures were conducted. In FIG. 2, the compounds are shown as follows.

Tetrachloroethylene: PCE
Trichloroethylene: TCE
2,2-Dichloro-1,1,1-trifluoroethane: F123
2-Chloro-1,1,1,2-tetrafluoroethane: F124
2-Chloro-1,1,1-trifluoroethane: F133a
Pentafluoroethane: F125
1,1,1,2-Tetrafluoroethane: F134a
Hydrogen fluoride: HF
Hydrogen chloride: HCl The apparatus shown in FIG. 2 is basically constructed by four gas phase reactors A, B, C and D capable of holding catalysts different from each other, a first distillation tower, a purification system for purifying a gas containing pentafluoroethane and 1,1,1,2-tetrafluoroethane separated from the top of a second distillation tower, and a third distillation tower for separating intermediate compounds such as HCFC-133a and unreacted hydrogen fluoride separated from the bottom of the second distillation tower.

In FIG. 2, reactions for producing pentafluoroethane are performed in reactors A and B. First, starting material tetrachloroethylene (PCE) (31) is introduced into the reactor A. In the reactor A, a catalyst optimal for the reaction is filled. Simultaneously, hydrogen fluoride (60) separated in the third distillation tower is introduced as (32) into the reactor A through a hydrogen fluoride circulating line. Hydrogen fluoride can be newly added and introduced, if desired. In the reactor A, reactions shown by the hereinbefore-mentioned formulae 1 and 2 take place and reactions shown by the hereinbefore-mentioned formulae 3 and 4 partially take place, whereby a first product (33) containing HCl, intermediates HCFC-123, HCFC-124 and HFC-125, and unreacted hydrogen fluoride is produced. The first product (33) is joined with a second product (37), a third product (43) and a fourth product (46) which are described later, and introduced as (51) into a first distillation tower 5.

Into the reactor B, HCFC-124 (56) separated in the purification system is introduced as (34) (in FIG. 2, ① shows that (56) and (34) are connected, ② shows that (58) and (44) are connected, and ③ shows that (59) and (35) are connected), HCFC-123/HF (59) separated in the third distillation tower 7 is introduced as (35), and a part of hydrogen fluoride (HF) (60) separated from the bottom of the third distillation tower 7 is circulated and introduced as (36). The reactor B is also filled with a catalyst optimal for the reaction. In the reactor B, reactions shown by the hereinbefore-mentioned formulae 3 and 4 take place and a second product (37) containing HCl, objective HFC-125 and unreacted HCFC-123, HCFC-124 and hydrogen fluoride is produced. The second product (37) is joined with gases from other reactors and introduced as (51) into the first distillation tower 5. On the other hand, reactions for producing 1,1,1,2-tetrafluoroethane are performed in reactors C and D. Into the reactor C, starting material trichloroethylene (TCE) (41) is introduced, and newly added hydrogen fluoride (40) and circulated hydrogen fluoride (42) are introduced. In the reactor C, a reaction shown by the hereinbefore-mentioned formula 5 mainly takes place to produce a third product (43) containing HCl, intermediate HCFC-133a and unreacted hydrogen fluoride and the third product (43) is joined with gases from other reactors and introduced as (51) into the first distillation tower 5.

Into the reactor D, HCFC-133a/HF (58) separated in the third distillation tower 7 is introduced as (44) and circulated hydrogen fluoride (60) is introduced as (45). A reaction shown by the hereinbefore-mentioned formula 6 mainly takes place to produce a fourth product (46) containing HCl, objective HFC-134a, unreacted HCFC-133a and hydrogen fluoride and the fourth product (46) is joined with gases from other reactors and introduced as (51) into the first distillation tower 5.

The first product (33), the second product (37), the third product (43) and the fourth product (46) are joined and the joined product (51) is introduced into the first distillation tower 5. From the top of the first distillation tower 5, a first top fraction (52) mainly comprising hydrogen chloride is eluted. From the bottom of the first distillation tower 5, 2,2-dichloro-1,1,1-trifluoroethane, 2-chloro-1,1,1,2-tetrafluoroethane, pentafluoroethane, 2-chloro-1,1,1-trifluoroethane, 1,1,1,2-tetrafluoroethane and hydrogen fluoride are mainly separated as a first bottom fraction (53).

The first bottom fraction (53) is introduced into the second distillation tower 6 and from the top of the second distillation tower 6, pentafluoroethane, 1,1,1,2-tetrafluoroethane, 2-chloro-1,1,1,2-tetrafluoroethane and hydrogen fluoride are mainly eluted as a second top fraction (54). This second top fraction (54) is supplied to the purification system and separated into HFC-134a/HFC-125 (55), HCFC-124 (56) and hydrogen fluoride. The purification system contains a fourth distillation tower (not shown). HCFC-124 and hydrogen fluoride each is circulated. From the bottom of the second distillation tower 6, 2,2-dichloro-1,1,1-trifluoroethane, 2-chloro-1,1,1-trifluoroethane and hydrogen fluoride are mainly separated as a second bottom fraction (57) and the second bottom fraction (57) is introduced into the third distillation tower 7.

In the third distillation tower 7, HCFC-133a/HF are separated as a third top fraction (58) from the top and this fraction is circulated to the reactor D. HCFC-123/HF (59) are drawn out from the side-cut plate provided upper than the feed plate of the third distillation tower 7, and circulated to the reactor B. From the bottom of the third distillation tower 7, hydrogen fluoride (60) is recovered and this is reused by circulating it to each of the reactors A, B, C and D according to necessity.

An example of operation according to the above-described method is described below by referring to the apparatus shown in FIG. 2.

Assuming that the flow rate of the joined product (51) is 100 (kg/hr), the mass ratio (mass %) of each component in process lines (31) to (37), (40) to (47), and (51) to (60) is shown in Tables 3 and 4.

TABLE 3

| | (31) | (32) | (33) | (34) | (35) | (36) | (37) | (40) | (41) | (42) | (43) | (44) | (45) | (46) | (47) |
|---|---|---|---|---|---|---|---|---|---|---|---|---|---|---|---|
| HFC-125 (F125) | 0.00 | 0.00 | 0.35 | 0.00 | 0.00 | 0.00 | 1.35 | 0.00 | 0.00 | 0.00 | 0.00 | 0.00 | 0.00 | 0.01 | 0.00 |
| HCFC-124 (F124) | 0.00 | 0.00 | 0.97 | 5.10 | 0.00 | 0.00 | 4.10 | 0.00 | 0.00 | 0.00 | 0.01 | 0.01 | 0.00 | 0.04 | 0.26 |
| HCFC-123 (F123) | 0.00 | 0.01 | 0.65 | 0.00 | 0.80 | 0.00 | 0.23 | 0.00 | 0.00 | 0.02 | 0.01 | 0.01 | 0.07 | 0.03 | 0.00 |
| HFC-134a (F134a) | 0.00 | 0.00 | 0.00 | 0.03 | 0.00 | 0.00 | 0.01 | 0.00 | 0.00 | 0.00 | 0.05 | 0.00 | 0.00 | 3.07 | 0.06 |
| HCFC-133a (F133a) | 0.00 | 0.00 | 0.00 | 0.31 | 0.00 | 0.00 | 0.33 | 0.00 | 0.00 | 0.00 | 3.57 | 29.85 | 0.00 | 26.27 | 0.00 |
| HF | 0.00 | 4.57 | 3.38 | 0.45 | 4.64 | 1.35 | 6.14 | 3.97 | 0.00 | 5.20 | 7.32 | 3.61 | 32.24 | 35.23 | 0.13 |
| HCl | 0.00 | 0.00 | 1.61 | 0.00 | 0.00 | 0.00 | 0.56 | 0.00 | 0.00 | 0.00 | 2.25 | 0.00 | 0.00 | 1.13 | 0.00 |
| PCE | 2.53 | 0.00 | 0.00 | 0.00 | 0.00 | 0.00 | 0.00 | 0.00 | 0.00 | 0.00 | 0.00 | 0.00 | 0.00 | 0.00 | 0.00 |
| TCE | 0.00 | 0.00 | 0.00 | 0.00 | 0.00 | 0.00 | 0.00 | 0.00 | 4.02 | 0.00 | 0.00 | 0.00 | 0.00 | 0.00 | 0.00 |
| Others | 0.00 | 0.00 | 0.15 | 0.06 | 0.00 | 0.00 | 0.04 | 0.00 | 0.00 | 0.02 | 0.03 | 0.65 | 0.00 | 0.65 | 0.00 |
| Total | 2.53 | 4.58 | 7.11 | 5.96 | 5.45 | 1.35 | 12.76 | 3.97 | 4.02 | 5.25 | 13.25 | 34.12 | 32.31 | 66.43 | 0.45 |

TABLE 4

| | (51) | (52) | (53) | (54) | (55) | (56) | (57) | (58) | (59) | (60) |
|---|---|---|---|---|---|---|---|---|---|---|
| HFC-125 (F125) | 1.72 | 0.33 | 1.39 | 1.39 | 1.39 | 0.00 | 0.00 | 0.00 | 0.00 | 0.00 |
| HCFC-124 (F124) | 5.38 | 0.00 | 5.38 | 5.37 | 0.01 | 5.10 | 0.01 | 0.01 | 0.00 | 0.00 |
| HCFC-123 (F123) | 0.91 | 0.00 | 0.91 | 0.00 | 0.00 | 0.00 | 0.91 | 0.01 | 0.80 | 0.10 |
| HFC-134a (F134a) | 3.20 | 0.00 | 3.20 | 3.19 | 3.10 | 0.03 | 0.00 | 0.00 | 0.00 | 0.00 |
| HCFC-133a (F133a) | 30.16 | 0.00 | 30.16 | 0.31 | 0.00 | 0.31 | 29.85 | 29.85 | 0.00 | 0.00 |
| HF | 52.21 | 0.00 | 52.21 | 0.60 | 0.01 | 0.45 | 51.61 | 3.61 | 4.64 | 43.35 |
| HCl | 5.55 | 5.55 | 0.00 | 0.00 | 0.00 | 0.00 | 0.00 | 0.00 | 0.00 | 0.00 |
| PCE | 0.00 | 0.00 | 0.00 | 0.00 | 0.00 | 0.00 | 0.00 | 0.00 | 0.00 | 0.00 |
| TCE | 0.00 | 0.00 | 0.00 | 0.00 | 0.00 | 0.00 | 0.00 | 0.00 | 0.00 | 0.00 |
| Others | 0.86 | 0.00 | 0.86 | 0.19 | 0.13 | 0.06 | 0.68 | 0.65 | 0.00 | 0.03 |
| Total | 100.00 | 5.88 | 94.12 | 11.06 | 4.64 | 5.96 | 83.06 | 34.12 | 5.45 | 43.49 |

INDUSTRIAL APPLICABILITY

As described above, the amount of a stabilizer contained in tetrachloroethylene can be reduced by using the purification method of the present invention. The purification method of the present invention is preferably used particularly for tetrachloroethylene containing a hydroxyl group-containing aromatic compound such as phenol or cresol.

However, it can be used also for tetrachloroethylene containing an amine group-containing aromatic compound. Furthermore, when pentafluoroethane is produced starting from tetrachloroethylene reduced in the hydroxyl group-containing aromatic compound, the catalyst used in the production process can have a long life and the pentafluoroethane can be produced efficiently and profitably.

Further, when the production process of a hydrofluorocarbon according to the present invention is used, a step for the separation of a product need not be provided every reactor and the products in the reactors are joined and then distilled in a distillation tower. The objective HFC-134a and HFC-125 and the by-product HCl are each recovered as a product and other intermediates and unreacted starting materials are circulated to respective steps and re-used, so that the process conditions in a continuous operation can be stabilized, the process control can be facilitated, the equipment can be simplified, and the energy consumption unit can be reduced as compared with conventional production processes.

Furthermore, when the production process of a hydrofluorocarbon according to the present invention is used, pentafluoroethane or 1,1,1,2-tetrafluoroethane and a hydrofluorocarbon such as difluoromethane, trifluoromethane, 1,2-difluoroethane or 1,1,1-trifluoroethane can be simultaneously produced.

The invention claimed is:

1. A process for producing pentafluoroethane, comprising the following three steps:
   (1) a step of reducing the amount of a hydroxyl group-containing aromatic compound contained in tetrachloroethylene by using a purification method comprising contacting tetrachloroethylene containing, as a stabilizer, a hydroxyl group-containing aromatic compound with a zeolite having an average pore size of 4.2 to 11 Å and a carbonaceous adsorbent having an average pore size of 3.4 to 11 Å, in a liquid phase, to reduce the amount of said stabilizer;
   (2) a step of reacting HF with said tetrachloroethylene reduced in the amount of the hydroxyl group-containing aromatic compound through the step (1), in the presence of an alumina-chromia catalyst in a gas phase to obtain a mixed gas containing 1,1-dichloro-2,2,2-trifluoroethane and 1-chloro-1,2,2,2-tetrafluoroethane; and
   (3) a step of reacting HF with the mixed gas containing 1,1-dichloro-2,2,2-trifluoroethane and 1-chloro-1,2,2,2-tetrafluoroethane obtained in the step (2), in the presence of an alumina-chromia catalyst in a gas phase to obtain pentafluoroethane.

2. A process according to claim 1, wherein the step (2) is performed using said tetrachloroethylene reduced in the amount of the hydroxyl group-containing aromatic compound to 30 mass ppm or less through the step (1).

3. A process according to claim 1 or 2, wherein the hydroxyl group-containing aromatic compound is at least one selected from the group consisting of phenol, cresol, 2,6-di-t-butyl-p-cresol and aminomethylphenol.

4. A process for producing a hydrofluorocarbon, comprising (A) a step of reacting hydrogen fluoride with a halogenated alkene and/or a halogenated alkane in the presence of a fluorination catalyst in a reaction zone to produce a first hydrofluorocarbon, (B) a step of reacting hydrogen fluoride with halogenated alkene and/or a halogenated alkane in the presence of a fluorination catalyst in another reaction zone to produce a second hydrofluorocarbon, and (C) a step of joining and then distilling the products obtained in the steps (A) and (B) to obtain the first hydrofluorocarbon and the second hydrofluorocarbon,
   wherein the step (A) comprises a step (1) of reacting hydrogen fluoride with tetrachloroethylene in the presence of a fluorination catalyst in a first reaction zone to produce a gas containing 2,2-dichloro-1,1,1-trifluoroethane and/or 2-chloro-1,1,1,2-tetrafluoroethane, and a step (2) of reacting hydrogen fluoride with a gas containing 2,2-dichloro-1,1,1-trifluoroethane and/or 2-chloro-1,1,1,2-tetrafluoroethane in the presence of a fluorination catalyst in a second reaction zone to produce a gas containing pentafluoroethane,
   wherein the tetrachloroethylene used in the step (1) is obtained from a step of reducing the amount of a hydroxyl group-containing aromatic compound contained in tetrachloroethylene by using a purification method comprising contacting tetrachloroethylene containing, as a stabilizer, a hydroxyl group-containing aromatic compound with a zeolite having an average pore size of 4.2 to 11 Å and a carbonaceous adsorbent having an average pore size of 3.4 to 11 Å, in a liquid phase, to reduce the amount of said stabilizer.

5. A process according to claim 4, wherein the step (B) is to react hydrogen fluoride with trichloroethylene and/or 2-chloro-1,1,1-trifluoroethane in the presence of a fluorination catalyst to produce 1,1,1,2-tetrafluoroethane as the second hydrofluorocarbon.

6. A process according to claim 4 or 5, wherein the step (B) comprises a step (3) of reacting hydrogen fluoride with trichloroethylene in the presence of a fluorination catalyst in a third reaction zone to produce a gas containing 2-chloro-1,1,1-trifluoroethane, and a step (4) of reacting hydrogen fluoride with a gas containing 2-chloro-1,1,1-trifluoroethane in the presence of a fluorination catalyst in a fourth reaction zone to produce a gas containing 1,1,1,2-tetrafluoroethane.

7. A process according to claim 4, wherein the step (C) is to join and then distill the gas containing pentafluoroethane obtained in the step (A) and the gas containing 1,1,1,2-tetrafluoroethane obtained in the step (B).

8. A process according to claim 4, wherein the step (A) comprises a step (1) of reacting hydrogen fluoride with tetrachloroethylene in the presence of a fluorination catalyst in a first reaction zone to obtain a gas containing hydrogen chloride, 2,2-dichloro-1,1,1-trifluoroethane, 2-chloro-1,1,1,2-tetrafluoroethane, pentafluoroethane and hydrogen fluoride and a step (2) of reacting hydrogen fluoride with a gas containing 2,2-dichloro-1,1,1-trifluoroethane and/or 2-chloro-1,1,1,2-tetrafluoroethane in the presence of a fluorination catalyst in a second reaction zone to obtain a gas containing hydrogen chloride, pentafluoroethane, 2,2-dichloro-1,1,1-trifluoroethane, 2-chloro-1,1,1,2-tetrafluoroethane and hydrogen fluoride, the step (B) comprises a step (3) of reading hydrogen fluoride with trichloroethylene in the presence of a fluorination catalyst in a third reaction zone to obtain a gas containing hydrogen chloride, 2-chloro-1,1,1-trifluoroethane and hydrogen fluoride and a step (4) of reading hydrogen fluoride with a gas containing 2-chloro-1,1,1-trifluoroethane in the presence of a fluorination catalyst in a fourth reaction zone to obtain a gas containing hydrogen chloride, 1,1,1,2-tetrafluoroethane, 2-chloro-1,1,1-trifluoroethane and hydrogen fluoride, and the step (C) comprises a step (5) of joining the gases obtained in said steps (1) to (4), introducing the joined gas into a distillation tower, and then distilling the gas to obtain pentafluoroethane and 1,1,1,2-tetrafluoroethane.

9. A process according to claim 4 or 8, wherein said fluorination catalyst is a supported or bulk catalyst mainly comprising a trivalent chromium oxide.

10. A process according to claim 8, wherein in all of the first to fourth reaction zones, the reaction pressure is from atmospheric pressure to 0.9 MPa.

11. A process according to claim 8 or 10, wherein the pressure in the second reaction zone is higher than the pressure in the first reaction zone, and the pressure in the fourth reaction zone is higher than the pressure in the third reaction zone.

12. A process according to claim 8, wherein said step (5) is to join the gases obtained in the steps (1) to (4) and introduce the joined gas into a first distillation tower to separate hydrogen chloride, 2-chloro-1,1,1-trifluoroethane, 2-chloro-1,1,1,2-tetrafluoroethane, pentafluoroethane and/or 1,1,1,2-tetrafluoroethane from the top of said distillation tower and separate hydrogen fluoride, 2,2-dichloro-1,1,1-trifluoroethane and/or 2-chloro-1,1,1-trifluoroethane from the bottom.

13. A process according to claim 12, wherein hydrogen fluoride, 2,2-dichloro-1,1,1-trifluoroethane and/or 2-chloro-1,1,1-trifluoroethane separated from the bottom of the first distillation tower are circulated to the reaction step.

14. A process according to claim 13, wherein hydrogen fluoride, 2,2-dichloro-1,1,1-trifluoroethane and/or 2-chloro-1,1,1-trifluoroethane separated from the bottom of the first distillation tower are introduced into a second distillation tower, purified by separation and then circulated to the reaction step.

15. A process according to claim 14, wherein hydrogen fluoride separated in the second distillation tower is circulated to at least one reaction zone of the first to fourth reaction zones.

16. A process according to claim 14, wherein the gas containing 2,2-dichloro-1,1,1-trifluoroethane, separated in the second distillation tower is circulated to the second reaction zone.

17. A process according to claim 14, wherein the gas containing 2-chloro-1,1,1-trifluoroethane, separated in the second distillation tower is circulated to the fourth reaction zone.

18. A process according to claim 12, wherein hydrogen chloride, 2-chloro-1,1,1-trifluoroethane, 2-chloro-1,1,1,2-tetrafluoroethane, pentafluoroethane and/or 1,1,1,2-tetrafluoroethane separated from the top of the first distillation tower are introduced into a third distillation tower to obtain pentafluoroethane and 1,1,1,2-tetrafluoroethane from the top.

19. A process according to claim 18, wherein the gas obtained from the top of the third distillation tower is rich in 1,1,1,2-tetrafluoroethane.

20. A process according to any one of claims 8 and 12 to 19, wherein the pressure inside the distillation tower is from atmospheric pressure to 3 MPa.

21. A process according to claim 4 comprising (A) a step of reacting hydrogen fluoride with at least one member selected from the group consisting of tetrachloroethylene, 2,2-dichloro-1,1,1-trifluoroethane and 2-chloro-1,1,1,2-tetrafluoroethane in the presence of a fluorination catalyst to produce pentafluoroethane, (B) a step of reacting hydrogen fluoride with trichloroethylene and/or 2-chloro-1,1,1-trifluoroethane in the presence of a fluorination catalyst to produce 1,1,1,2-tetrafluoroethane, and (C) a step of joining the products obtained in the steps (A) and (B), introducing these products into a distillation tower, separating a gas mainly containing hydrogen chloride from the top, separating a gas containing pentafluoroethane and 1,1,1,2-tetrafluoroethane from the bottom, and distilling the gas obtained from the bottom to obtain pentafluoroethane and 1,1,1,2-tetrafluoroethane.

22. A process according to claim 21, wherein the step (A) comprises a step (1) of reacting hydrogen fluoride with tetrachloroethylene in the presence of a fluorination catalyst in a first reaction zone to produce a gas containing 2,2-dichloro-1,1,1-trifluoroethane and/or 2-chloro-1,1,1,2-tetrafluoroethane, and a step (2) of reacting hydrogen fluoride with a gas containing 2,2-dichloro-1,1,1-trifluoroethane and/or 2-chloro-1,1,1,2-tetrafluoroethane in the presence of a fluorination catalyst in a second reaction zone to produce a gas containing pentafluoroethane.

23. A process according to claim 21 or 22, wherein the step (B) comprises a step (3) of reacting hydrogen fluoride with trichloroethylene in the presence of a fluorination catalyst in a third reaction zone to produce a gas containing 2-chloro-1,1,1-trifluoroethane, and a step (4) of reacting hydrogen fluoride with a gas containing 2-chloro-1,1,1-trifluoroethane in the presence of a fluorination catalyst in a fourth reaction zone to produce a gas containing 1,1,1,2-tetrafluoroethane.

24. A process according to claim 21, wherein the step (A) comprises a step (1) of reacting hydrogen fluoride with tetrachloroethylene in the presence of a fluorination catalyst in a gas phase in a first reaction zone to produce a gas containing hydrogen chloride, 2,2-dichloro-1,1,1-trifluoroethane, 2-chloro-1,1,1,2-tetrafluoroethane, pentafluoroethane and hydrogen fluoride and a step (2) of reacting hydrogen fluoride with a gas containing 2,2-dichloro-1,1,1-trifluoroethane and/or 2-chloro-1,1,1,2-tetrafluoroethane in the presence of a fluorination catalyst in a gas phase in a second reaction zone to produce a gas containing hydrogen chloride, pentafluoroethane, 2,2-dichloro-1,1,1-trifluoroethane, 2-chloro-1,1,1,2-tetrafluoroethane and hydrogen fluoride, the step (B) comprises a step (3) of reacting hydrogen fluoride with trichloroethylene in the presence of a fluorination catalyst in a gas phase in a third reaction zone to produce a gas containing hydrogen chloride, 2-chloro-1,1,1-trifluoroethane and hydrogen fluoride and a step (4) of reacting hydrogen fluoride with a gas containing 2-chloro-1,1,1-trifluoroethane in the presence of a fluorination catalyst in a gas phase in a fourth reaction zone to produce a gas containing hydrogen chloride, 1,1,1,2-tetrafluoroethane, 2-chloro-1,1,1-trifluoroethane and hydrogen fluoride, and the step (C) comprises a step (5) of joining the gases obtained in said steps (1) to (4), introducing these gases into a distillation tower, separating a gas mainly containing hydrogen chloride from the top, separating a gas containing pentafluoroethane and 1,1,1,2-tetrafluoroethane from the bottom, and distilling the gas obtained from the bottom to obtain pentafluoroethane and 1,1,1,2-tetrafluoroethane.

25. A process according to claim 21 or 24, wherein the fluorination catalyst is a supported or bulk catalyst mainly comprising a trivalent chromium oxide.

26. A process according to claim 24, wherein in all of the first to fourth reaction zones, the reaction pressure is from atmospheric pressure to 0.9 MPa.

27. A process according to claim 24 or 26, wherein the pressure in the second reaction zone is higher than the pressure in the first reaction zone, and the pressure in the fourth reaction zone is higher than the pressure in the third reaction zone.

28. A process according to claim 24, wherein the step (5) comprises a step of joining the gases obtained in the steps (1) to (4), introducing these gases into a first distillation tower, separating hydrogen chloride from the top of said distillation tower, and separating a gas mainly containing 2-chloro-1,1,1-trifluoroethane, 2,2-dichloro-1,1,1-trifluoroethane, 2-chloro-1,1,1,2-tetrafluoroethane, pentafluoroethane, 1,1,1,2-tetrafluoroethane and/or hydrogen fluoride from the bottom.

29. A process according to claim 28, wherein the gas mainly containing 2-chloro-1,1,1-trifluoroethane, 2,2-dichloro-1,1,1-trifluoroethane, 2-chloro-1,1,1,2-tetrafluoroethane, pentafluoroethane, 1,1,1,2-tetrafluoroethane and/or hydrogen fluoride, separated from the bottom of the first distillation tower is introduced into a second distillation tower to separate pentafluoroethane, 1,1,1,2-tetrafluoroethane and/or 2-chloro-1,1,1,2-tetrafluoroethane from the top and separate 2-chloro-1,1,1-trifluoroethane, 2,2-dichloro-1,1,1-trifluoroethane and/or hydrogen fluoride from the bottom.

30. A process according to claim 29, wherein the gas mainly containing 2-chloro-1,1,1-trifluoroethane, 2,2-dichloro-1,1,1-trifluoroethane and/or hydrogen fluoride, separated from the bottom of the second distillation tower is introduced into a third distillation tower to separate and purify respective components and then, these components are circulated to the reaction step.

31. A process according to claim 30, wherein the hydrogen fluoride separated in the third distillation tower is circulated to at least one reaction zone of said first to fourth reaction zones.

32. A process according to claim 30, wherein the gas mainly containing 2,2-dichloro-1,1,1-trifluoroethane, separated in the third distillation tower is circulated to the second reaction zone.

33. A process according to claim 30, wherein the gas mainly containing 2-chloro-1,1,1-trifluoroethane, separated in the third distillation tower is circulated to the fourth reaction zone.

34. A process according to claim 29, wherein the gas separated from the top of the second distillation tower is rich in 1,1,1,2-tetrafluoroethane.

35. A process according to claim 29, wherein the gas containing pentafluoroethane, 1,1,1,2-tetrafluoroethane and/or 2-chloro-1,1,1,2-tetrafluoroethane, separated from the top of the second distillation tower is introduced into a fourth distillation tower to separate pentafluoroethane and 1,1,1,2-tetrafluoroethane from the top and separate 2-chloro-1,1,1,2-tetrafluoroethane from the bottom, and 2-chloro-1,1,1,2-tetrafluoroethane is circulated to the second reaction zone.

36. A process according to any one of claims 21, 24 and 28 to 35, wherein the pressure inside the distillation tower is from atmospheric pressure to 3 MPa.

* * * * *